United States Patent [19]

Buck et al.

[11] 4,263,363

[45] Apr. 21, 1981

[54] EMULSION-CONTAINING ABSORBENT ARTICLE HAVING IMPROVED WATER HOLDING CAPACITY

[75] Inventors: Charles E. Buck, Caldwell; Robert C. Roga, Spotswood, both of N.J.

[73] Assignee: Colgate-Palmolive Company, New York, N.Y.

[21] Appl. No.: 105,817

[22] Filed: Dec. 20, 1979

[51] Int. Cl.³ .......................... B32B 5/18; B32B 7/02
[52] U.S. Cl. .................................... 428/284; 128/284; 128/290 R; 428/286; 428/300; 428/311; 428/321; 521/905; 521/54; 521/55
[58] Field of Search .......................... 128/284, 290 R; 428/234, 235, 246, 260, 311, 284, 321, 286, 300; 521/905, 54, 55

[56] References Cited

U.S. PATENT DOCUMENTS

| | | | |
|---|---|---|---|
| 2,653,601 | 9/1953 | Morrison | 128/260 |
| 2,900,278 | 8/1959 | Powers et al. | 521/905 |
| 3,264,188 | 8/1966 | Gresham | 128/260 |
| 3,431,911 | 3/1969 | Meisel, Jr. | 428/311 |
| 3,464,413 | 9/1969 | Goldfarb et al. | 128/268 |
| 3,489,148 | 1/1970 | Duncan et al. | 128/284 |
| 3,585,998 | 6/1971 | Hayford et al. | 128/284 |
| 3,586,648 | 6/1971 | Sambeth et al. | 521/905 |
| 3,783,872 | 1/1974 | King | 128/290 R |
| 3,826,674 | 7/1974 | Schwarz | 428/311 |
| 3,896,807 | 7/1975 | Buchalter | 128/261 |
| 3,898,143 | 8/1975 | Assarsson et al. | 128/284 |
| 3,900,378 | 8/1975 | Yen et al. | 128/284 |
| 3,978,855 | 9/1976 | McRae et al. | 428/311 |
| 4,062,451 | 12/1977 | Gander | 428/192 |
| 4,069,177 | 1/1978 | Smith | 128/285 |
| 4,076,663 | 2/1978 | Masuda et al. | 128/285 |
| 4,115,332 | 9/1978 | Verbanac | 128/285 |
| 4,117,222 | 9/1978 | Holst et al. | 128/284 |

Primary Examiner—William J. Van Balen
Attorney, Agent, or Firm—Norman Blumenkopf; Herbert S. Sylvester; Murray M. Grill

[57] ABSTRACT

A water-in-oil emulsion at a ratio of 80/20 or less when incorporated into a water absorbing material (such as a polyurethane sponge) will aid in retaining water that may be subsequently added to the absorbing material. The effect is believed due to the increased viscosity of the emulsion when water is added. The effect is particularly useful for improving urine retention of diapers, such as disposable diapers or similar articles.

11 Claims, No Drawings

EMULSION-CONTAINING ABSORBENT ARTICLE HAVING IMPROVED WATER HOLDING CAPACITY

BACKGROUND OF THE INVENTION

1. Field of the Invention

The present invention relates to absorbent articles such as diapers and particularly to water-in-oil emulsion concentrates as the absorbing material. More particularly, the present invention relates to absorbent articles which are capable of absorbing and retaining thereon large amounts of aqueous fluids such as urine in the form of a stable and highly viscous water-in-oil emulsion wherein the absorbing material is a concentrated water-in-oil emulsion forming composition carried on an oleophilic substrate.

2. Discussion of the Prior Art

Many attempts have been described in the patent literature to prepare super absorbent materials, i.e. materials which are capable of absorbing many times their weight of water or various body fluids. For example, the use of hydrogels for enhancing the absorbing media of absorbing articles, such as disposable diapers, has been described in U.S. Pat. Nos. 3,783,872 to King, 3,898,143 and 3,901,236 to Assarsson et al and 3,900,378 to Yen et al; Silane crosslinked acrylate interpolymers as the super absorbing media has been described in U.S. Pat. No. 4,062,451 to Gander; and various forms of modified starches have been described in the following U.S. Pat. Nos. 4,069,177 to Smith, 4,076,663 to Masuda et al, 4,115,332 to Young et al, and 4,117,222 to Holtz et al.

It is not believed, however, that the use of water-in-oil emulsion concentrates as the absorbing media, per se, have been described in the literature for this purpose. It is known, however, that water-in-oil emulsions can form viscous fluids with the viscosity increasing with increasing water content. The properties of emulsions have been extensively described in the literature and reference is made to the following publications: Becher, P., "Emulsions, Theory and Practice", Reinhold, New York, 1965 (Standard reference book on emulsions); Adamson A.W., "Physical Chemistry of Surfaces", 3rd Edition, John Wiley, New York, 1976 (Chapter 12 provides an overview of emulsions and foams); Prince, L.N., "Micro-Emulsions, Theory and Practice", Academic Press, New York, 1977 (review of modern emulsion technology); Lissant, K.J. and Mayhan, K.G., J. Colloid Interface Sci, 42, 201–208, January, 1973 (geometry of internal phase at high ratios); Groves, M.J., Chem. Ind. 12,417–423, June 17, 1978 (reviews recent concepts of spontaneous emulsification); Lin, T.J., et al, J. Soc. Cosmetic Chem. 26, 121–139, March, 1975 (Phase inversion temperature, HLB values and emulsion behavior).

There has also been patent literature of the use of mineral oils and mineral oil emulsions in various articles which are designed to come into contact with the human body. U.S. Pat. No. 3,264,188 to Gresham describes a sanitary impregnated tissue for proctological use in which a pure pharmaceutical grade mineral oil of low viscosity containing a fatty acid soap of an organic base as a non-toxic, non-allergenic emulsifier is impregnated throughout one or more plies of absorbent creped cellulosic tissue. This tissue is described as having ability, when used as a wipe, to pick up, absorb, and hold fecal matter from the skin and wiped areas while transferring a thin film of the emulsifier-containing mineral oil to the skin.

U.S. Pat. No. 3,464,413 to Goldfarb, et al describes absorbent dressings having a multiplicity of discrete rupturable microcapsules containing various agents including emulsified oils. U.S. Pat. No. 3,489,148 to Duncan, et al describes a diaper having an absorptive pad and a thin diaper fibrous material top sheet. On one face of the top sheet a discontinuous film of an oleaginous moisture barrier material is applied to at least the central portions thereof for application to the skin of an infant. The patentee teaches that mineral oil can be mixed with a crystalline material such as triglycerides of higher fatty acids to increase its viscosity. A diaper containing pressure rupturable capsules containing formulations based on mineral oil and other ingredients such as isopropyl myristate is described in U.S. Pat. No. 3,585,998 to Hayford, et al.

U.S. Pat. No. 2,653,601 to E. M. Morrison relates to gloves designed and intended for use as an accessory for the treatment of the skin of the hands of the wearer. The glove includes a relatively heavy layer of a porous material including sheet rubber or lightweight plastic. The porous material is adapted to hold within its pores or interstices a cream or lotion. However, in practice, the cream or lotion is placed on the hands of the wearer and the glove primarily provides a massaging function.

U.S. Pat. No. 3,896,807 to Buchalter relates to an article such as a piece of apparel, e.g. glove, or an applicator pad, impregnated with the oil phase of a cream formulation which upon the addition of moisture thereto forms a skin-soothing cream. This patent also mentions other patents disclosing articles of apparel and applicator pads for use in applying therapeutic creams, lotions or oils to the skin. In this patent the oil phase is in the form of a dry non-oily solid including from about 1 to 99% of an oily material and from about 99 to 1% of an emulsifier. When the oil phase impregnated in the articles is mixed with water a cream or a less viscous lotion is formed. Either water-in-oil or oil-in-water emulsions may be formed.

SUMMARY OF THE INVENTION

It is an object of the present invention to provide absorbent articles, especially disposable diapers, having an improved capacity for immobilizing aqueous fluids, such as urine, which come into contact with the absorbent articles.

It is a further object of the present invention to provide a disposable diaper having an emulsion concentrate capable of absorbing and surrounding urine coming into contact therewith with a continuous oil phase which may optionally be designed to promote soothing and healing of irritated skin by contacting the skin with the external oil phase of the formed water-in-oil emulsion.

A still further object of the present invention is to provide a disposable diaper in which the urine absorbing or immobilizing material is an emulsion concentrate capable of very rapidly forming a stable and highly viscous water-in-oil emulsion after being contacted with urine.

In its broadest aspect, these and other objects of the present invention are accomplished by an absorbent article for aqueous fluids in which the absorbing or aqueous fluid immobilizing material is an emulsion concentrate capable of forming a viscous stable water-in-oil emulsion upon addition to the concentrate of an aqueous fluid, the concentrate comprising an oily substance and a surfactant and preferably also an emollient, the ratio of oily substance to surfactant being in the range of at least about 50 parts oily substance to about 50 parts surfactant. To promote the formation of the water-in-oil emulsion and to reduce the amount of time and the amount of energy necessary for the stable viscous emulsion to form, the concentrate is applied to a substrate as a thin layer having a very high surface area. To this end, the preferred substrate for the absorbing article is an oleophilic material such as an oleophilic foam, especially an oleophilic polyurethane foam.

To further aid in the formation of the water-in-oil emulsion, the surfactant material is selected to have an HLB value in the range of from about 2 to about 7 or less. The oily emulsion concentrate should be capable of immobilizing up to about 50 times its weight of aqueous fluid in the form of a stable thickened viscous water-in-oil emulsion especially within a period of from about 5 to about 20 seconds after the concentrate is contacted with the aqueous fluid.

Although the preferred application of the absorbent articles are as disposable diapers, other uses such as bandages, sanitary napkins, wipes, articles of clothing, sporting apparel and the like are also in the scope of the present invention.

The invention will be better understood from the following detailed description and specific embodiments.

DETAILED DESCRIPTION OF THE INVENTION

The absorbent articles of the invention are capable of absorbing by firmly immobilizing large amounts of aqueous fluids in the form of stable viscous water-in-oil emulsions. The absorbing or fluid immobilizing material is an oily concentrate capable of forming a viscous stable water-in-oil emulsion rapidly upon being contacted with an aqueous fluid, especially an aqueous body fluid and most especially urine. The concentrate is substantially uniformly distributed over at least a portion of the surface of an oleophilic substrate, such as an oleophilic polyurethane foam or a non-woven fibrous web formed from oleophilic filamentary material.

The oily self-emulsifying concentrate of the invention includes at least one surfactant having an HLB value in the range of about 2-7, preferably about 3-6 and a low to medium viscosity oil or hydrocarbon solvent such that when an aqueous fluid is added to the concentrate a water-in-oil emulsion will form with a viscosity and thickness of the emulsion increasing as the amount of fluid added increases. The concentrate will further include from about 0 to about 10% by weight, preferably from about 1 to about 10% by weight, more preferably from about 1 to about 5% by weight of a co-surfactant and/or an emollient.

The weight ratio of the oil or hydrocarbon solvent to the surfactant will range from about 50:50 to about 95:5, preferably from about 70:30 to about 92:8 and more preferably from about 80:20 to about 90:10 and most preferably from about 82:18 to about 88:12. Therefore, the concentrate will preferably include from about 5 to about 30% by weight, more preferably from about 8 to 20% by weight, most preferably from about 10 to about 15% by weight of at least one surfactant having an HLB value in the range of from about 2 to about 7, preferably from about 3 to about 6 and capable of forming a water-in-oil emulsion; from about 70 to about 92% by weight, more preferably from about 80 to 90% by weight, and most preferably from about 82 to 88% by weight of a low to medium viscosity oil substance or hydrocarbon solvent and from about 0 to about 10% by weight, preferably from about 1 to about 10% by weight and more preferably from about 1 to about 5% by weight of a co-surfactant or emollient.

Any surfactant material having the required HLB value such that it is capable of forming a water-in-oil emulsion can be used in the present invention. Generally, anionic as well as non-ionic surfactants can be used. However, in view of their higher degree of tolerance in contact with the skin the non-ionic surfactants are preferred.

In general, suitable water-in-oil emulsifiers or surfactants having HLB values in the range of from about 2 to about 7, preferably from about 3 to 6 and most preferably from about 4 to about 6 are well known and are described in, for example, "The Atlas HLB System" (4th printing) 1963 by Atlas Chemical Industries, Inc. Examples of suitable emulsifiers include sorbitan fatty acid esters, for example, the laurate, palmitate, stearate, tristearate and sesquioleate sorbitan fatty esters such as sold under the trademarks ARLACEL and SPAN: polyoxyethylene alcohols such as sold under the trademarks VOLPO, BRIJ and STANDAMUL: mono and diglycerides such as sold under the trademarks ATMOS and ATMUL: and polyoxyethylene sorbitol esters. Mixtures of two or more surfactants having a weight average HLB value within the specified range are especially preferred and generally will form more stable emulsions capable of imbibing larger amounts of aqueous fluids in less time.

Low (Saybolt viscosity 55–65 seconds) or medium (Saybolt viscosity 80–95 seconds) viscosity mineral oil is the preferred oily component of the concentrates. Obviously, any other oil substance or hydrocarbon solvent forming a water-in-oil emulsion with the surfactant emulsifier and which is non-irritating to the human skin can be used in the present invention. However, especially for disposable diapers which come into contact with human skin, the use of mineral oil is preferred because of its low toxicity. In addition to its capacity for forming water-in-oil emulsions, mineral oil provides a soothing effect when in contact with human skin. Other materials which can be used to replace part or all of the mineral oil include, for example, lanolin, silicone oils, castor oil derivatives, triglycerides, isopropyl myristate, as well as other oily substances such as, for example, vegetable oils, safflower oil and the like. In addition, for applications of absorbent articles which are not intended for coming into contact with the human skin such as where the emulsion concentrate is included in an intermediary layer hydrocarbon solvents which form water-in-oil emulsions can be used as the oily substance.

In addition to the surfactant emulsifier and oily substance the concentrates of the present invention can also include for the purpose of promoting compatibility between the emulsifier and oily substance and for generally aiding in the formation of the water-in-oil emulsion one or more emollients or co-surfactants which function as keying agents. A preferred emollient keying agent is glycerine, especially low viscosity glycerine. Other suitable keying agents include, for example, propylene glycol, mannitol and similar polyhydric substances, or even water. The use of keying agents is especially preferred for aiding in the emulsification when the surfactant emulsifier or mixture of surfactants has an HLB or total HLB value of less than about 7.0, and no lower than about 5.3.

Emollients, such as lanolin and lanolin derivatives, fatty acid methyl esters, fatty alcohols and the like both aid in the formation of the emulsions as well as providing a soothing effect when they come into contact with the skin. Accordingly, the use of such emollients in the emulsion concentrates is especially preferred.

The oily concentrates can be prepared by any conventional procedure for mixing the emulsifier and oily substance as well as any additional ingredients including the co-surfactants, emollients or other keying agents and any other additives such as preservatives, perfumes, germicides, anti-bacteriostats, humectants, etc. The ingredients can all be placed in a vessel and mixed together or can be mixed sequentially in any order.

After the emulsion concentrate is formed, it is impregnated into a substrate. In the present invention it is important that the emulsion concentrate have as high a surface area and be as thin as possible so that there will be a maximum area for the liquid to be absorbed to contact the concentrate and minimize the energy required to form the emulsion. In this regard it has now been disdiscovered, and this is an essential and critical feature of the present invention, that a porous oleophilic substrate having a large surface area such as an oleophilic polyurethane foam which may be reticulated (open or intercommunicating cells) or non-reticulated (closed cells) is used as the substrate. To provide the necessary surface area, the oleophilic substrate should have a large void or free volume on the order of at least 50%, preferably at least 80%, more preferably at least 90% of the total volume. Other highly suitable materials for forming the substrate include polyesters, polypropylene, blends of polyurethanes and polypropylenes as well as normally non-oleophilic materials which have been modified to render them oleophilic. Both polyester polyurethanes and polyether polyurethanes can be used although the former are preferred. Other foam materials may include, for example, air-blown latex foams. Porous sponge-like materials from oleophilic substances provide the required high surface areas and additionally are easily wetted by the concentrate and can be fabricated with sufficient flexibility, resiliency and dimensional stability to be used to form absorbent articles such as diapers, bed innerpads and the like which are subjected to vigorous stresses and pressure due to the movements of the body.

Other porous absorbent support materials which can be used to form the absorbent articles of this invention include, for example, nonwoven webs, specifically needle punched nonwovens, resin bonded nonwovens, spunbonded nonwovens and melt-blown non-wovens, absorbent fluffs such as oleophilic cellulose fluffs and sheets of absorbent oleophilic minerals and clays.

The oleophilic polyurethane foam substrates may be polyester polyurethanes, polyether polyurethanes or polyether-ester polyurethanes. Reticulated foams are especially preferred, but non-reticulated foams can also be used. The preferred polyurethane foams are those having a void volume of at least 90% preferably at least 95%, especially preferably at least 97% of the total volume and a porosity of at least 50 pores per inch, preferably at least 70 pores per inch, more preferably from about 80 to about 110 pores per inch. A specific example of a suitable low bulk density, high void volume (90% or more) oleophilic polyester type polyurethane foam substrate is SCOTT FOAM manufactured by Scott Paper Product Company. SCOTT FOAM is available as a reticulated and non-reticulated foam. Both foams are available in thickness of from 1/32 inch and higher and with a porosity of from 10 to over 100 pores per inch. The preferred porosity is from about 80 pores per inch up to about 100 pores per inch. SCOTT FOAMS are also advantageous because they are soft, resilient and dimensionally stable, capable of withstanding pressures of 0.5 psi.

Another preferred form of the substrate includes meltblown webs of synthetic filaments especially polyester filaments and polypropylene filaments. These melt-blown webs have at least about 90% free volume. Melt-blown polyester webs formed from polyester filaments of 1 to 2 micron diameter filaments and melt-blown polypropylene webs formed from polypropylene filaments having diameters in the range of from about 3 to 4 microns are examples of preferred types of melt-blown webs. The polyesters are especially preferred because they tend to be softer than the polypropylene webs and are also more effective.

The amount of the self-emulsifying concentrate applied to the substrate will vary depending upon the nature of the substrate and the nature of the concentrate as well as the intended application. For example, when used to form disposable diapers, the absorbent product should be capable of immobilizing at least three urinations and therefore should have a capacity to immobilize about 150 milliliters of urine. It is therefore a simple matter to determine the required quantity of the concentrate by simple experimentation.

As noted above, the use of an oleophilic substrate allows the self-emulsifying oily concentrate to be applied to the substrate as a thin film. In particular, the amount of concentrate applied should be just that sufficient to wet the walls of the substrate. In the case of non-woven webs, for example, the amount of concentrate impregnated into the web need only be that amount sufficient to coat the filaments making up the web. In the case of the foam materials the amount of oily concentrate impregnated into the foam need merely be that amount which will wet the structure forming the boundaries of the cells of the foam but should not fill the cells themselves.

If the amount of the self-emulsifying concentrate is substantially greater than the amount necessary for wetting the walls of the substrate various problems could arise. For example, if the thickness of the concentrate is more than, for example, a few tenths of a millimeter, the aqueous fluid may have difficulty penetrating through the surface of the concentrate to form the emulsion. Therefore, for many applications the amount of energy input for mixing the aqueous fluid with the oily concentrate to form the emulsion would be too great or the amount of time required for forming the emulsion may be too high. This is especially the case, for instance, with disposable diapers wherein it is important that the force of the urine impinging on the absorbent product be itself sufficient to cause the emulsification to take place or at least coupled with the energy imparted by the movement of the user of the diaper. For instance, during the night an infant wearing a disposable diaper will not necessarily make any movements during urination and it is therefore mandatory that the urine be immediately immobilized, e.g. within a period of about 10-20 seconds or less, without any additional energy input.

A further disadvantage of applying an excess amount of the oil concentrate is with respect to the expansion of the concentrate as it forms the viscous emulsion upon contact with the aqueous fluid. Naturally, if a substantial amount of the void space of the substrate is consumed by the oily concentrate there will be no room for the absorbent product to retain the emulsion as it expands to essentially the volume of the fluid to be immobilized. That is, since the self-emulsifiable concentrates of the subject invention are capable of absorbing up to about 30 times their weight, preferably from about 5 to 25 times their weight, more preferably from about 8 to 15 times their weight of aqueous fluid it is apparent that the volume of the emulsion would be primarily the water phase (as the dispersed phase) with the oil phase (as the external, continous phase) constituting a minor percentage of the total volume. It is acceptable, however, if a small amount of the emulsion comes into contact with the body of the user since the external oil phase provides a soothing effect against the skin.

In its simplest embodiment the absorbent articles of the invention can be in the form of an absorbent pad or wipe in which an oleophilic substrate is impregnated with the self-emulsifying emulsion concentrate. Or the absorbent pad can form a component of, or a layer or core of any conventional absorbent article, especially disposable or single use absorbent articles such as disposable diapers, sanitary napkins, tampons, bandages, sporting goods (for example, head and wrist sweat bands, cap or helmet liners, etc.), gloves or glove linings, and the like. These absorbent articles are primarily intended to absorb and immobilize aqueous body fluids such as urine, blood, perspiration, wound exudates, catemenial discharges, etc. However, the absorbent articles are useful wherever it is intended to absorb and immobilize any aqueous fluid.

The oleophilic substrate of the absorbent pad should be sufficiently resilient and flexible so that it can conform to the part of the body to which it is applied, can be fabricated into any desired shape and configuration, and is dimensionally stable, i.e. will be able to repeatedly return to its original shape and configuration afer withdrawal of external forces (for example, from the natural movements of the wearer when the absorbent article is used as apparel, e.g. diapers, etc. or from simply being squeezed, as with the pressure of baby sitting on the diaper). In addition, the substrate must be capable of retaining its shape and still be resilient and flexible under the load of the weight of the absorbed aqueous fluid. In view of the generally very low bulk densities of the preferred foam and nonwoven substrates, the weight of the absorbed fluid will usually be at least twenty or thirty or more times the weight of the substrate for a fully loaded absorbent pad, i.e. a pad which has absorbed and immobilized fluid up to its full capacity. If, for example, under the weight of the emulsion (which is approximately the same as the weight of the absorbed and immobilized aqueous fluid for a fully loaded absorbent article) and external forces the cells of a foam substrate were to collapse or the thickness of a nonwoven web substrate was to decrease, the absorbing capacity would decrease in an amount corresponding to the loss of volume. This would in turn create a risk of leakage or a reduction in the absorbing capacity. For instance, when used as the, or as part of the, absorbent core of a disposable diaper, it is essential that the diaper be snug-fitting yet sufficiently flexible and thin that it will be able to change its shape as the body of the user moves from one position to another.

The absorbent articles of the invention therefore include the self-emulsifying, water-in-oil emulsion forming, emulsion concentrate impregnated in the form of a thin film wetting the walls of an absorbent flexible and resilient, oleophilic substrate, such that the article is capable of being held in form-fitting contact with an animal body whereby the emulsion concentrate is in fluid flow communication with aqueous body fluids exuded or discharged by the animal body either directly or after passing through a body-contacting cover or top sheet and optionally one or more additional layers.

A disposable diaper, which may be for infants and young babies, as well as for incontinent adults, or a sanitary napkin or tampon, or similar article will usually include a body contacting, liquid permeable top sheet, a liquid impervious bottom sheet and one or more intermediate layers of or containing the absorbent material.

The liquid permeable body contacting top or cover sheet can be used, if desired, to also wrap around the outside edges and under the liquid impervious bottom sheet. Any woven or nonwoven cellulosic fibrous web or other liquid permeable material having sufficient wet-strength and mechanical strength such that it is capable of resisting breakage or disintegration when in contact with the body fluids or when subjected to stress, can be used. The cover sheet must have fast strike-through of the aqueous fluid without itself becoming wet. Most conventional diaper top sheets are satisfactory.

Very good results with regard to softness, smoothness, strike-through and dryness have been obtained when the top sheet is formed from a thin sheet, about 1/32 to about 1/16 inch, of the same type of foam as may be used as the oleophilic substrate, but, of course, without the emulsion concentrate. This untreated foam top sheet can be attached to a foam or other oleophilic substrate by any suitable adhesive or by heat fusing. It is also possible to cause the emulsion concentrate to penetrate though only a portion of the thickness of a foam substrate such that the impregnated portion forms the absorbent pad and the non-impregnated portion functions as the top sheet. For example, starting with a foam sheet that is ¼ inch thick, the amount of emulsion concentrate can be limited to impregnate through only three-fourths of the thickness. The absorbent pad will then be 3/16 inch and the top sheet 1/16 inch.

The top sheet can be of the same general configuration as or substantially larger than the absorbent pad; in the latter case the top sheet can be used to wrap the sides and under the impervious back sheet.

The liquid impervious back or bottom sheet may be formed from any water insoluble film-forming plastic material such as polyethyhlene, polypropylene, polyurethane, polyamide (e.g. nylon), polyester and the like. The back sheet should be as thin as possible, generally on the order of about 1 mil being satisfactory.

In place of a separate film layer attached to the bottom of the absorbent pad a fluid impervious material may be coated onto the bottom of the absorbent pad. Coating compositions based on any of the above-mentioned film-forming plastic materials, or any other coating composition which provides a liquid impervious, non-toxic coating, which is inert to the oleophilic substrate and emulsion concentrate, as well as the emulsion itself, may be used.

In still another embodiment the impervious back sheet may be an integral part of the oleophilic substrate. For example, it is well known to form oleophilic foams having a liquid impervious skin formed on one surface. For example, the foam can be formed on a metal surface which can be heated to a temperature above the melting point of the foam material to melt the surface of the foam in contact with the heated metal surface to form a thin skin. Or the bottom surface of the foam may be flame bonded or softened by a solvent to form the thin liquid impervious skin.

In any case, the liquid permeable top sheet, absorbent core and liquid impervious bottom sheet should be chosen and secured to each other such that the elasticity of the respective layers will match each other. This is important to assure good fit of the absorbent article, especially for disposable diapers and similar absorbent articles which are subjected to a large amount of wiggling movement, pressure and stress in use.

In addition to the emulsion concentrate containing absorbent pad, it is within the scope of the invention for the absorbent core to include an additional absorbent material such as conventional cellulosic wadding, wood fluff, etc. The amount and absorbing capacity of the absorbent core will be determined on the basis of the intended use. When used in disposable diapers the amount of absorbent and capacity of the absorbent pad will be sufficient to immobilize at least two and preferably three urinations, or about 150 millimeters.

In forming the absorbent pad to be used as the absorbent core of disposable diapers, bed pads and similar articles, it is not essential that the emulsion concentrate extend over the entire area of the oleophilic substrate. It is sufficient for the emulsion concentrate to be located within a central portion of the substrate and away from at least one, preferably at least two, and most preferably all four of the sides of the substrate. By leaving one or more edges of the absorbent pad free of the emulsion concentrate it becomes simple to bond the absorbent pad to the other layers of the absorbent article since it is difficult to find adhesives or bonding methods which are effective in the presence of oily substances.

In a particularly preferred arrangement of layers of an absorbent article according to the invention the absorbent emulsion concentrate containing pad is used in combination with a needle punched fabric absorbent sheet either between the absorbent pad and liquid permeable top sheet or between the absorbent pad and liquid impervious bottom sheet. The absorbent sheet provides extra absorbing capacity for any excess emulsified urine if the absorbent pad becomes saturated and provides a support function for the absorbent pad. This tends to reduce the likelihood of the absorbent pad from compressing under the weight of the emulsion or at least to provide additional loft or bulk to the absorbent article so that it may retain its form-fitting configuration, especially when the absorbent article is a disposable diaper.

Preferred materials for the absorbent sheet include needle punched fabrics formed from polypropylene or polyester or mixtures thereof in a density range of from about 1 to about 30 ounces per square yard. In addition plural absorbent sheets can be used in any suitable arranged, for example a paper fluff sheet next to the liquid impervious bottom sheet and a needle punched fabric sheet which is receptive to oily materials between the absorbent pad and paper fluff sheet. The needle punched fabric may be formed integrally with the paper fluff or they may be separate or laminated to each other or the paper fluff sheet may be above the absorbent pad and the needle punched fabric below the absorbent pad. By using both an emulsion receptive needle punched fabric and a non-emulsified urine receptive paper fluff or other suitable material it can be appreciated that any excess emulsified or non-emulsified urine (or other aqueous liquid) will be retained in the absorbent core of the absorbent article.

In the preferred embodiment of the present invention the absorbent article is a disposable diaper comprising a liquid permeable body contacting top sheet, a liquid impermeable bottom sheet and an absorbent core comprising the absorbent emulsion concentrate containing olephilic substrate between the top sheet and bottom sheet. The preferred diaper configuration is the conventional boxpleated disposable diaper having self-sticking adhesive tabs attached thereto. Such diapers are described, for example, in U.S. Pat. No. 4,051,853 to Egan, the disclosure of which is incorporated herein by reference. However, any diaper configuration which will fit snugly in use can be adopted for the absorbent articles of the invention.

In the following non-limiting examples of the invention, all parts and percents are on a weight basis unless otherwise noted. The absorbent pads are rated as "good", "fair" or "unsatisfactory" as follows:

If the absorbent pad can immobilize at least 30 parts of urine per part of emulsion concentrate it is rated as "good"; if the pad can immobilize from 20 to 30 parts of urine per part of emulsion concentrate it is rated as "fair"; if the pad can only immobilize less than 20 parts of urine per part of emulsion concentrate it is rated as "unsatisfactory." The determination of immobilization is made as follows:

A quantity of synthetic urine at 37° C. is slowly poured from a height 1 inch above an absorbent pad measuring 4 inches × 6 inches onto the center of the pad within a 1½ inch diameter circle. Ten seconds after pouring is finished the pad is picked up at the short edge and held in a vertical position. The amount of the emulsion which leaks from the absorbent pad is measured at the end of 5 seconds, 30 seconds, 1 minute, 5 minutes, 15 minutes, 30 minutes and 1 hour. The urine is considered to be immobilized in the pad if the amount of emulsion which leaks from the pad is within the following limits:

| Time | Amount (parts per part of urine absorbed) |
|---|---|
| 5 seconds | 0.0000 |
| 30 seconds | <0.0001 |
| 1 minute | <0.0005 |
| 5 minutes | <0.001 |
| 15 minutes | <0.002 |
| 30 minutes | <0.005 |
| 1 hour | <0.01 |

EXAMPLE 1

A self-emulsifying concentrate is prepared by blending the following ingredients:

12% ethoxylated lauryl alcohol (2 moles ethylene oxide per mole lauryl alcohol) (Standamul LA-2, Henkel & Cie)

3% ethoxylated lauryl alcohol (1 mole ethylene oxide per mole lauryl alcohol) (Standamul LA-1, Henkel & Cie)

3% glycerine
82% mineral oil, very light viscosity, NF
Standmul LA-2 has an HLB value of 5.7.
Standmul LA-1 has an HLB value of 3.8.
The mixture has an HLB value of 5.3.

A diaper top sheet is prepared by laminating a 1 mil polyethylene backing sheet to a 4 inch×4 inch×¼ inch retriculated polyester type polyurethane foam having 100 pores per linear inch and 97% free volume (SCOTT FOAM) and then applying a spun bonded polypropylene top sheet. An absorbent pad is formed by impregnating the polyurethane foam with 1 part of the emulsion concentrate per part of foam substrate. The absorbent pad has a "good" rating and, in fact, is able to immobilize almost 30 parts of urine per part of the emulsion concentrate. The pad has an oily feel and substantially no urine odor even when left to stand for 3 hours at room temperature.

EXAMPLE 2

This example shows that with water-in-oil forming emulsifiers having relatively high HLB values the glycerine keying agent can be omitted from the emulsion concentrate.

An emulsion concentrate is prepared from 12 parts ethoxylated oleyl alcohol (3 moles ethylene oxide) (Volpo-3, Croda Inc.) (HLB=6.6); 3 parts fatty alcohol glycerol ether (Cremophor WO-A, BASF Wyandotte) (HLB=4.8 to 5.8) and 85 parts mineral oil, medium viscosity, NF. The two mixed emulsifiers have a total HLB value of 6.3.

Following the procedure of Example 1 using the same SCOTT FOAM reticulated polyester type polyurethane foam 100 ppi, an absorbent pad is prepared by impregnating a 4 inch×4 inch×¼ inch sheet of the SCOTT FOAM with 1 part of concentrate per part of the foam sheet. The resulting absorbent pad is capable of immobilizing up to 30 parts of urine per part of the emulsion concentrate. Even after absorbing the urine the pad maintains an oily feel and does not acquire a urine odor. This shows that the urine forms the discontinuous water phase of a stable water-in-oil emulsion.

EXAMPLE 3

Examples 1 and 2 are each repeated except that the polyurethane foam substrate is replaced by a nonwoven web of meltblown polyester filaments (1–2 udiameter) having a void volume of about 90%. In both cases the absorbent pad rates good.

What we claim is:

1. An absorbent pad capable of immobilizing aqueous fluids as a stable viscous water-in-oil emulsion comprising a porous flexible resilient oleophilic substrate having a void volume of at least 50% of the total volume and an oily self-emulsifying emulsion concentrate comprising an oil or hydrocarbon solvent and at least one water-in-oil forming emulsifier having a total HLB value of from 2 to 7, the weight ratio of the oil or hydrocarbon solvent to emulsifier ranging from about 50:50 to about 95:5, said emulsion concentrate being impregnated over at least a portion of the oleophilic substrate as a thin film, said concentrate being present in an amount just sufficient to wet the walls of the porous substrate in the portion in which is is impregnated.

2. The absorbent pad of claim 1 wherein the oleophilic substrate is a polyurethane foam.

3. The absorbent pad of claim 2 wherein the polyurethane foam is a reticulated polyester polyurethane having from about 80 to about 100 pores per inch and from about 95 to about 97% free volume.

4. The absorbent pad of claim 1 which further comprises a liquid impervious layer on one major surface of the oleophilic substrate and a liquid permeable layer on the other major surface of the oleophilic substrate.

5. The absorbent pad of claim 2 wherein the polyurethane foam includes a liquid impervious skin formed from the polyurethane material on one surface of the foam.

6. The absorbent pad of claim 1 wherein the ratio of oil or hydrocarbon solvent to emulsifier is from about 67:33 to about 90:10.

7. An absorbent article capable of absorbing and immobilizing aqueous liquids in the form of a stable viscous water-in-oil emulsion comprising a liquid permeable top sheet, a liquid impervious bottom sheet and an absorbent core between the top and bottom sheets, said absorbent core comprising a porous oleophilic polyurethane foam substrate having at least 90% free volume and at least 50 pores per inch and impregnated therein, over at least a portion of the surface of the substrate, a self-emulsifying oily emulsion concentrate comprising from about 50 to about 95 parts of an oil or hydrocarbon solvent and from about 50 to 5 parts of at least one water-in-oil forming emulsifier having an HLB value of from about 2 to about 7, the amount of the emulsion concentrate being sufficient to wet the walls of the polyurethane foam substrate in the portion in which it is impregnated.

8. The absorbent article of claim 7 which is a disposable diaper and the emulsion concentrate further comprises from 0 to 10% by weight of the concentrate of at least one keying agent for promoting the formation of a water-in-oil emulsion when the concentrate is contacted with urine.

9. The disposable diaper of claim 8 wherein the emulsion concentrate comprises from about 80 to 90 percent of a low to medium viscosity mineral oil, from about 10 to 20% by weight of a mixture of emulsifiers having an HLB value of from about 3 o 6 and from 0 to 10% by weight of a keying agent selected from the group consisting of glycerin, propylene glycol, mannitol and water.

10. The disposable diaper of claim 9 wherein the polyurethane foam substrate comprises a reticulated polyesterpolyurethane, polyether-urethane or polyesteretherurethane foam having at least 97% free volume, from about 80 to 100 pores per inch, said foam substrate having a thickness of from about 1/32 inch to about ¼ inch.

11. The disposable diaper of claim 10 wherein the absorbent core further comprises at least one needle punched fabric layer adjacent to said foam substrate, said fabric layer being absoprtive to oleophilic liquids such as water-in-oil emulsions.

* * * * *